United States Patent
Wood et al.

(10) Patent No.: US 10,350,408 B2
(45) Date of Patent: Jul. 16, 2019

(54) INTERVENTIONAL MEDICAL SYSTEMS, ASSOCIATED ASSEMBLIES AND METHODS

(71) Applicant: Medtronic, Inc., Minneapolis, MN (US)

(72) Inventors: Rónán Wood, Galway (IE); Tomas K Kelly, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 490 days.

(21) Appl. No.: 15/140,565

(22) Filed: Apr. 28, 2016

(65) Prior Publication Data

US 2017/0312496 A1    Nov. 2, 2017

(51) Int. Cl.
| | | |
|---|---|---|
| *A61N 1/05* | (2006.01) | |
| *A61B 17/34* | (2006.01) | |
| *A61N 1/375* | (2006.01) | |

(52) U.S. Cl.
CPC .......... *A61N 1/057* (2013.01); *A61B 17/3468* (2013.01); *A61N 1/0573* (2013.01); *A61N 1/3756* (2013.01); *A61N 1/3758* (2013.01); *A61N 1/37518* (2017.08); *A61N 2001/058* (2013.01); *A61N 2001/0578* (2013.01)

(58) Field of Classification Search
CPC .. A61N 1/057; A61N 1/0573; A61N 1/37518; A61N 1/3758; A61N 2001/058; A61N 2001/0578; A61N 1/3756; A61B 17/3468; A61M 25/0082
See application file for complete search history.

(56) References Cited

U.S. PATENT DOCUMENTS

| | | | |
|---|---|---|---|
| 3,835,864 A | 9/1974 | Rasor et al. | |
| 5,250,071 A | 10/1993 | Palermo | |
| 5,261,916 A | 11/1993 | Engelson | |
| 7,344,553 B2 | 3/2008 | Opolski et al. | |
| 8,364,280 B2 | 1/2013 | Marnfeldt et al. | |
| 8,504,156 B2 | 8/2013 | Bonner et al. | |
| 8,548,605 B2 | 10/2013 | Ollivier | |
| 8,615,310 B2 | 12/2013 | Khairkhahan et al. | |
| 8,721,587 B2 | 5/2014 | Berthiaume et al. | |

(Continued)

OTHER PUBLICATIONS

U.S. Appl. No. 14/926,827, filed Oct. 27, 2015.

(Continued)

*Primary Examiner* — Eric J Rosen
*Assistant Examiner* — Chima U Igboko (57) ABSTRACT

A catheter inner assembly includes a receptacle with an interior contour configured to mate with a head and neck contour of a holding member of an implantable medical device; and a laterally facing opening of the receptacle has a profile matching a longitudinal profile of the head and neck. Thus, the opening allows only a properly oriented passage of the holding member therethrough, the passage being without deformation of holding member or opening. The inner assembly further includes a lock and release member useful for securing the device to the catheter, when the holding member has been passed through the receptacle's opening to mate with the receptacle's interior contour. The lock and release member may include an arcuate sidewall moveable between a first location, at which the sidewall overlays the laterally facing opening, and a second location, at which the sidewall is located proximal to the opening.

17 Claims, 7 Drawing Sheets

(56) References Cited

U.S. PATENT DOCUMENTS

| | | |
|---|---|---|
| 8,781,605 B2 | 7/2014 | Bomzin et al. |
| 8,903,513 B2 | 12/2014 | Ollivier |
| 8,945,145 B2 | 2/2015 | Tran et al. |
| 8,958,892 B2 | 2/2015 | Khairkhahan et al. |
| 9,205,225 B2 | 12/2015 | Khairkhahan et al. |
| 9,216,293 B2 | 12/2015 | Berthiaume et al. |
| 9,238,145 B2 | 1/2016 | Wenzel et al. |
| 2003/0181945 A1* | 9/2003 | Opolski ............. A61B 17/0057 606/206 |
| 2012/0095539 A1 | 4/2012 | Khairkhahan et al. |
| 2012/0172891 A1 | 7/2012 | Lee |
| 2012/0172892 A1 | 7/2012 | Grubac et al. |
| 2013/0035748 A1 | 2/2013 | Bonner et al. |
| 2013/0103047 A1 | 4/2013 | Steingisser et al. |
| 2014/0018818 A1 | 1/2014 | Somogyi et al. |
| 2014/0172034 A1 | 6/2014 | Bornzin et al. |
| 2014/0180306 A1 | 6/2014 | Grubac et al. |
| 2014/0249543 A1 | 9/2014 | Berthiaume et al. |
| 2014/0330219 A1 | 11/2014 | Quint |
| 2015/0051609 A1 | 2/2015 | Schmidt et al. |
| 2015/0051613 A1 | 2/2015 | Schmidt et al. |
| 2015/0051615 A1 | 2/2015 | Schmidt et al. |
| 2015/0094668 A1* | 4/2015 | Wood ................ A61M 25/0105 604/256 |
| 2015/0273212 A1 | 10/2015 | Berthiaume et al. |
| 2016/0015968 A1* | 1/2016 | Bonner ................ A61N 1/0592 606/129 |
| 2016/0059003 A1 | 3/2016 | Eggen et al. |

OTHER PUBLICATIONS

U.S. Appl. No. 14/598,346, filed Jan. 16, 2015.
U.S. Appl. No. 14/694,083, filed Apr. 23, 2015.
U.S. Appl. No. 14/696,009, filed Apr. 24, 2015.
U.S. Appl. No. 14/620,904, filed Feb. 12, 2015.
U.S. Appl. No. 14/548,958, filed Nov. 20, 2014.
U.S. Appl. No. 14/694,579, filed Apr. 23, 2015.
U.S. Appl. No. 62/281,312, filed Jan. 21, 2016.
(PCT/US2017/029822) PCT Notification of Transmittal of the International Search Report and the Written Opinion of the International Searching Authority, dated Nov. 3, 2017, 9 pages.

* cited by examiner

INTERVENTIONAL MEDICAL SYSTEMS, ASSOCIATED ASSEMBLIES AND METHODS

FIELD OF THE DISCLOSURE

The present disclosure pertains to interventional medical systems that include relatively compact implantable medical devices, and more particularly to assemblies of catheters that are configured to deliver the devices to an implant site.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site, for example, within a right ventricle RV of the heart.

Figure 1:
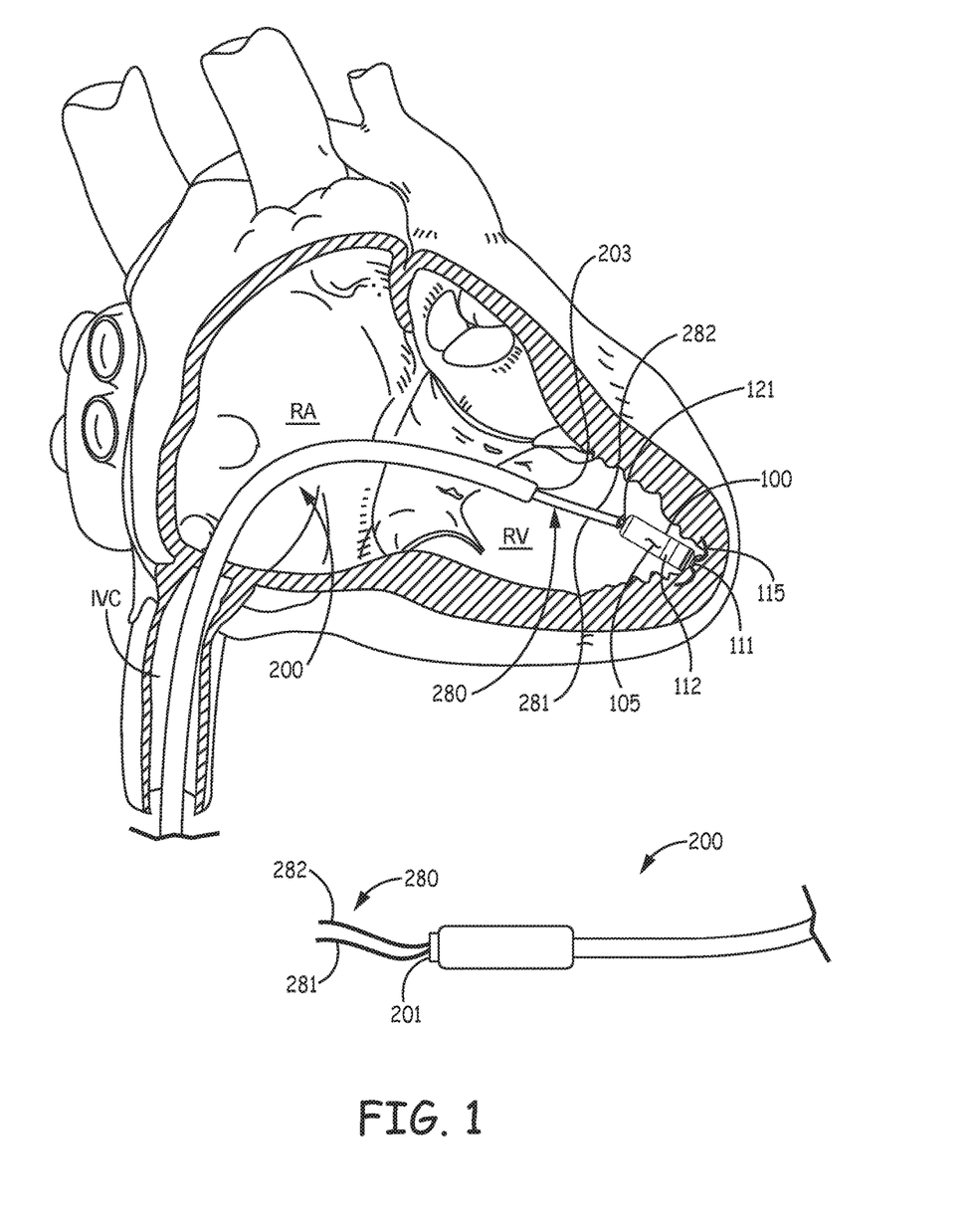
FIG. 1 is a schematic showing an exemplary relatively compact implantable medical device having been delivered from a catheter to an implant site.

FIG. 1 is a schematic showing an example of an implanted relatively compact implantable medical device 100. FIG. 1 illustrates medical device 100 having been delivered through a catheter 200, which an operator has maneuvered up through the inferior vena cava IVC and the right atrium RA into the right ventricle RV. Device 100 is shown deployed at an implant site in the right ventricular apex. Another potential cardiac implant site may be within an appendage of a right atrium RA, or within a coronary vein. Device 100 and catheter 200 may be similar to the device and tool, respectively, described in the commonly assigned United States Patent Application US 2015/0094668.

FIG. 1 further illustrates device 100 including a hermetically sealed enclosure 105 containing pulse generator electronics and a power source (not shown), pace/sense electrodes 111, 112 formed on an exterior surface of enclosure 105, and a fixation member, for example, formed from a plurality of elastically deformable fingers 115 mounted to a distal end of enclosure 105, in proximity to electrode 111, in order to fix, or secure electrode 111 against the endocardial surface at the implant site. Enclosure 105 is preferably formed from a biocompatible and biostable metal such as titanium overlaid with an insulative layer, for example, medical grade polyurethane or silicone, except where electrode 112 is formed as an exposed portion of the metal. An hermetic feedthrough assembly, such as any suitable type known to those skilled in the art, couples electrode 111 to the pulse generator contained within device enclosure 105. Device 100 is shown fixed at the implant site by fingers 115 of the fixation member thereof, but still secured to catheter 200 by a flexible tether 280, which extends out from a distal opening 203 of catheter 200, being joined to a holding member 121 of device 100. Thus, the operator, via tether 280, is able to test the fixation of device 100 at the implant site, and/or remove device 100 from the implant site for repositioning at a more suitable site, if necessary. Once satisfied with the implant of device 100, the operator can separate tether 280 from device 100, for example, by releasing an end of one length 281 of tether 280, and then pulling on an end of another length 282 of tether 280 to withdraw an entirety of length 282 proximally through delivery catheter 200 so that tether length 281 is pulled distally and through holding member 121.

Securing device 100 to catheter 200 with tether 280 is typically accomplished by a process in which tether 280 is looped through device holding member 121, after which first and second lengths 281, 282 of tether 280 are threaded through one or more lumens of catheter 200 such that opposing ends thereof protrude out from a proximal opening 201 of catheter 200. Because this process may be somewhat tedious, a manufacturer of device 100 and catheter 200 may secure the two together as a system, and provide the system to the operator in a single sterile package. However, due to shelf life considerations, the packaging of such a device separately from the associated catheter may be preferred, so that alternative means for securing the device to the catheter may be necessary to increase the ease by which an operator may load the device into the catheter at the time of an implant procedure.

SUMMARY

Embodiments of interventional medical systems, disclosed herein, include a relatively compact implantable medical device and a catheter, wherein a receptacle, which may be formed in a distal end of an inner assembly shaft of the catheter, has an interior contour configured to mate with a head and neck contour of a holding member of the device, and has a laterally facing opening with a profile that matches a longitudinal profile of the head and neck of the holding member. Thus, the laterally facing opening of the receptacle allows only properly oriented passage of the device holding member therethrough, and this passage is without deformation of either the device holding member or the laterally facing opening. The catheter inner assembly further includes a lock and release member useful for securing the device to the catheter, when the device holding member has been passed through the opening of the receptacle to mate with the interior contour of the receptacle. According to some embodiments of the catheter inner assembly, the lock and release member includes an arcuate sidewall in sliding engagement with the shaft so that the sidewall can be moved between a first location, at which the sidewall overlays the laterally facing opening of the receptacle, and a second location, at which the sidewall is located proximal to the opening. In some embodiments, a handle of the catheter includes a control member coupled to the lock and release member.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
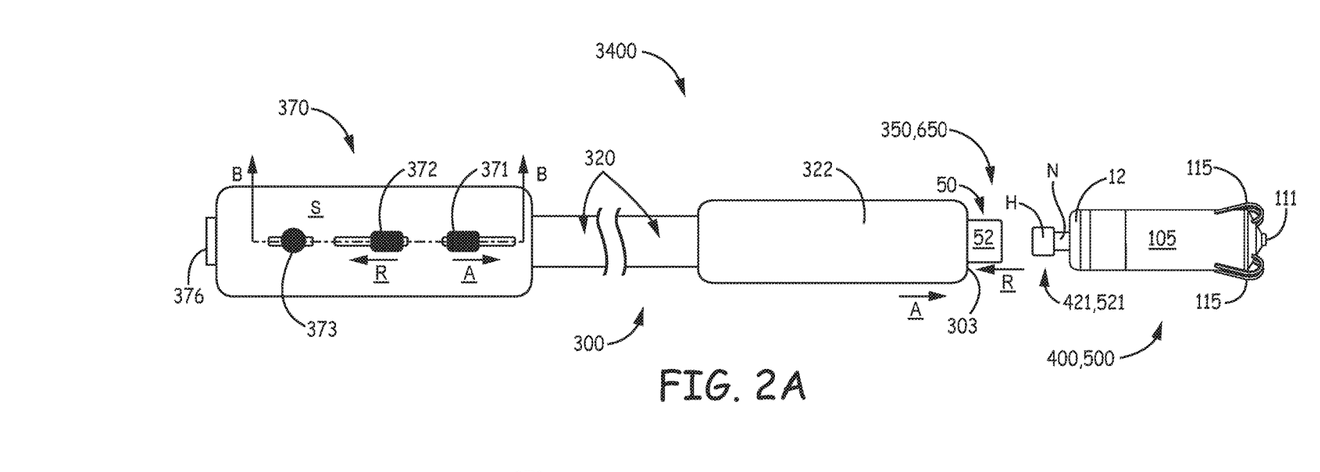
FIG. 2A is a plan view of an interventional medical system, according to some embodiments.
Figure 2B:
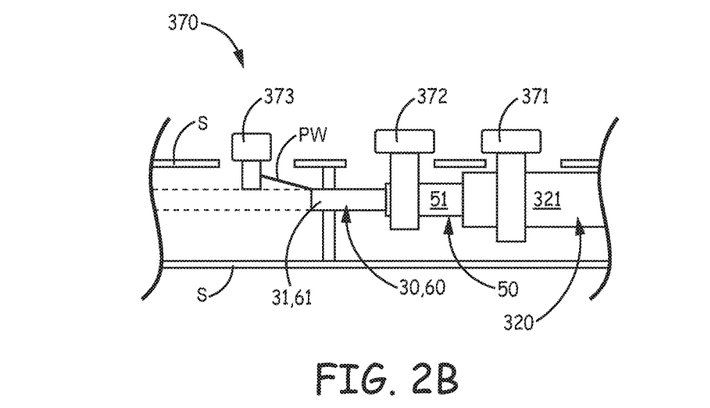
FIG. 2B is a schematic cross-section view through section line B-B of FIG. 2A.

FIG. 2A is a plan view of an interventional medical system 3400, according to some embodiments. FIG. 2A illustrates system 3400 including a catheter 300 and an implantable medical device 400, 500 (two types of embodiments described below), which is similar to device 100 described above, in conjunction with FIG. 1. FIG. 2A further illustrates catheter 300 including an elongate outer tubular member 320, an inner assembly 350, 650 (two types of embodiments described below), and a handle 370, wherein handle 370 includes a first control member 371 coupled to outer tubular member 371, and a second control member 372 coupled to a lock and release member 50 of inner assembly 350, 650, which will be described in greater detail below. According to the illustrated embodiment, inner assembly 350 extends within a lumen 302 (FIG. 5) of outer tubular member 320 and is in sliding engagement therewith, so that, when control member 371 is moved to a first position, a distal portion of inner assembly 350, 650 is contained within lumen 302, and, when control member 371 is moved to a second position, as shown in FIG. 2A, inner assembly 350, 650 protrudes distally from a distal-most opening 303 of lumen 302, which is defined at a distal end 322 of outer tubular member 320. FIG. 2B is a schematic cross-section view through section line B-B of FIG. 2A, in which proximal ends 321, 51 of outer tubular member 320 and lock and release member 50, respectively, are shown coupled to the corresponding control members 371, 372 within a shell S of handle 370. Handle 370 may be constructed from injection molded, relatively hard, medical grade plastic parts, according to methods known in the art.

Figure 3A:
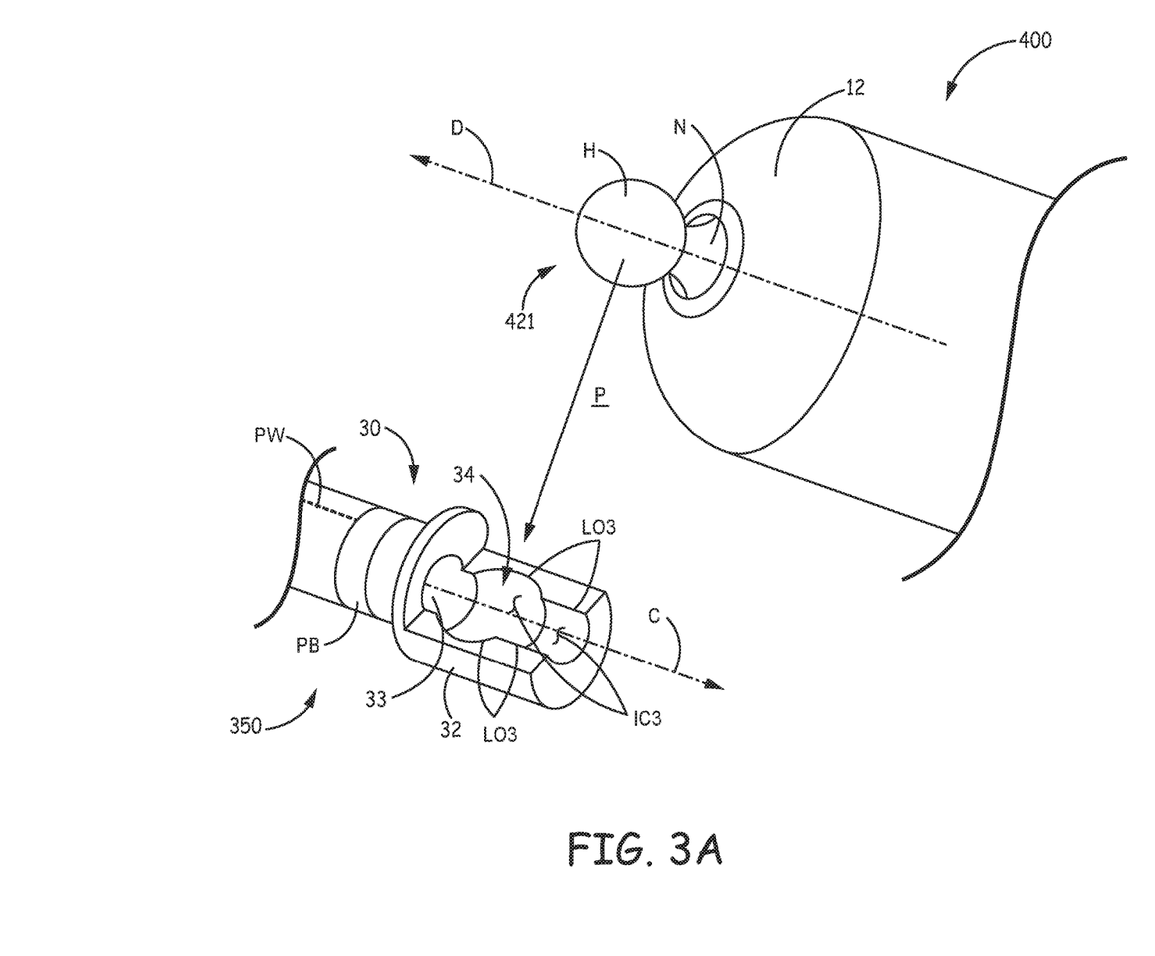
FIGS. 3A-B are a perspective views of a distal portion of a catheter assembly and a proximal portion of an associated implantable medical device, according to some embodiments.
Figure 3B:
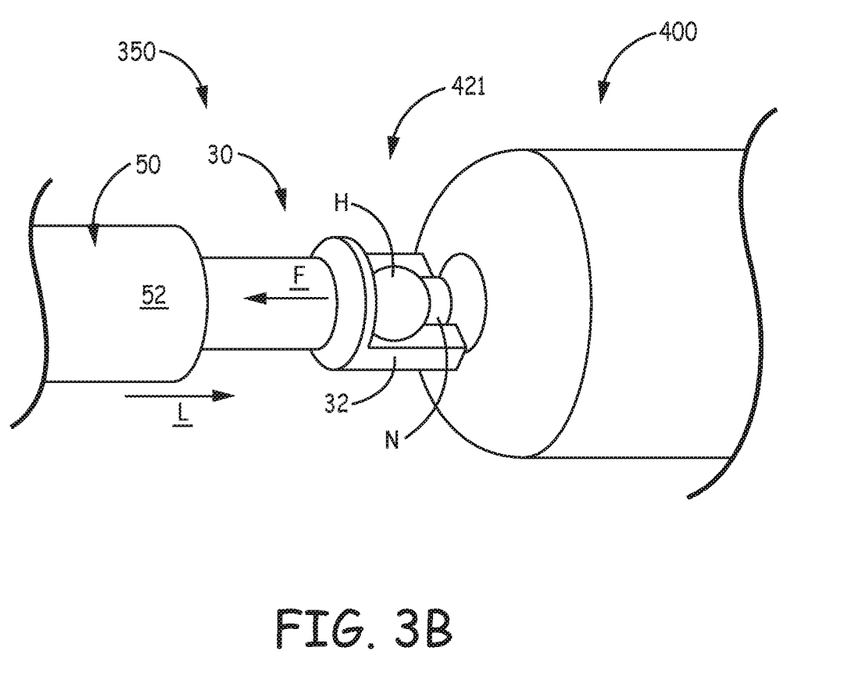

With further reference to FIG. 2A, medical device 400, 500 includes a holding member 421, 521 having a contour that forms a neck N and an enlarged head H, wherein neck N extends proximally from a proximal end 12 of device housing 105. FIGS. 3A-B are a perspective views of the distal portion of catheter inner assembly 350 and a proximal portion of medical device 400, according to some embodiments, in which device 400 is shown positioned relative to inner assembly 350, according to some methods for securing device 400 to catheter 300. FIGS. 3A-B show lock and release member 50 of catheter inner assembly 350 retracted, for example, by moving second control member 372 per arrow R of FIG. 2A, to expose a distal end 32 of an elongate shaft 30 of inner assembly 350. With reference to FIG. 2B, a proximal end 31 of shaft 30 is shown fixed to shell S of handle 370, such that second control member 372 may be employed to retract and advance lock and release member 50 relative to shaft 30. FIG. 3A illustrates distal end 32 of shaft 30 having a receptacle 34 formed therein to receive enlarged head H and neck N of device holding member 421, for example, as shown in FIG. 3B.

With further reference to FIG. 3A, receptacle 34 of shaft 30 has an interior contour IC3 configured to mate with the head and neck contour of device holding member 421, when holding member 421 is received therein. At least a portion of interior contour IC3 is shown being approximately hemispherical to mate with the spherical contour of holding member head H, according to some embodiments. FIG. 3A illustrates receptacle 34 including a laterally facing opening that has a profile LO3 matching a longitudinal profile of neck N and enlarged head H of holding member 421, wherein the longitudinal profile corresponds to that which extends parallel to a longitudinal axis D of device 400. A longitudinal axis C of catheter inner assembly shaft 30 is shown in FIG. 3A for reference, so that the descriptor "laterally facing" for the opening of receptacle 34 can be understood to mean facing in a direction approximately orthogonal to axis C. According to the illustrated embodiment, profile LO3 of the lateral facing opening of receptacle 34 matches the head and neck profile of holding member 421 so that the opening only allows a properly oriented passage of holding member 421 therethrough, for example, per arrow P. Furthermore, receptacle 34 is sized such that passage of holding member 421 through the laterally facing opening thereof and into mating contact with interior contour IC3 does not cause holding member 421 or receptacle opening to deform.

FIG. 3B illustrates a distal end of lock and release member 50 of inner assembly 350 being formed by an arcuate sidewall 52, which, in a retracted position, being located proximal to shaft distal end 32, allows passage of holding member 421 into and out from of receptacle 34. According to the illustrated embodiment, sidewall 52 is in sliding engagement around shaft 30, to be moved, per arrow L, from the retracted position to an advanced position, at which sidewall 52 overlays the laterally facing opening of receptacle 34 to secure device 400 to catheter 300. According to some methods, after securing device 400 in this manner, outer tubular member 320 may be advanced, per arrow A of FIG. 2A, relative to inner assembly 350 and the secured device 400, so that the distal portion of inner assembly 350 and secured device 400 are contained within lumen 302 of outer tubular member 320, for example, as described below in conjunction with FIG. 5.

Figure 4A:
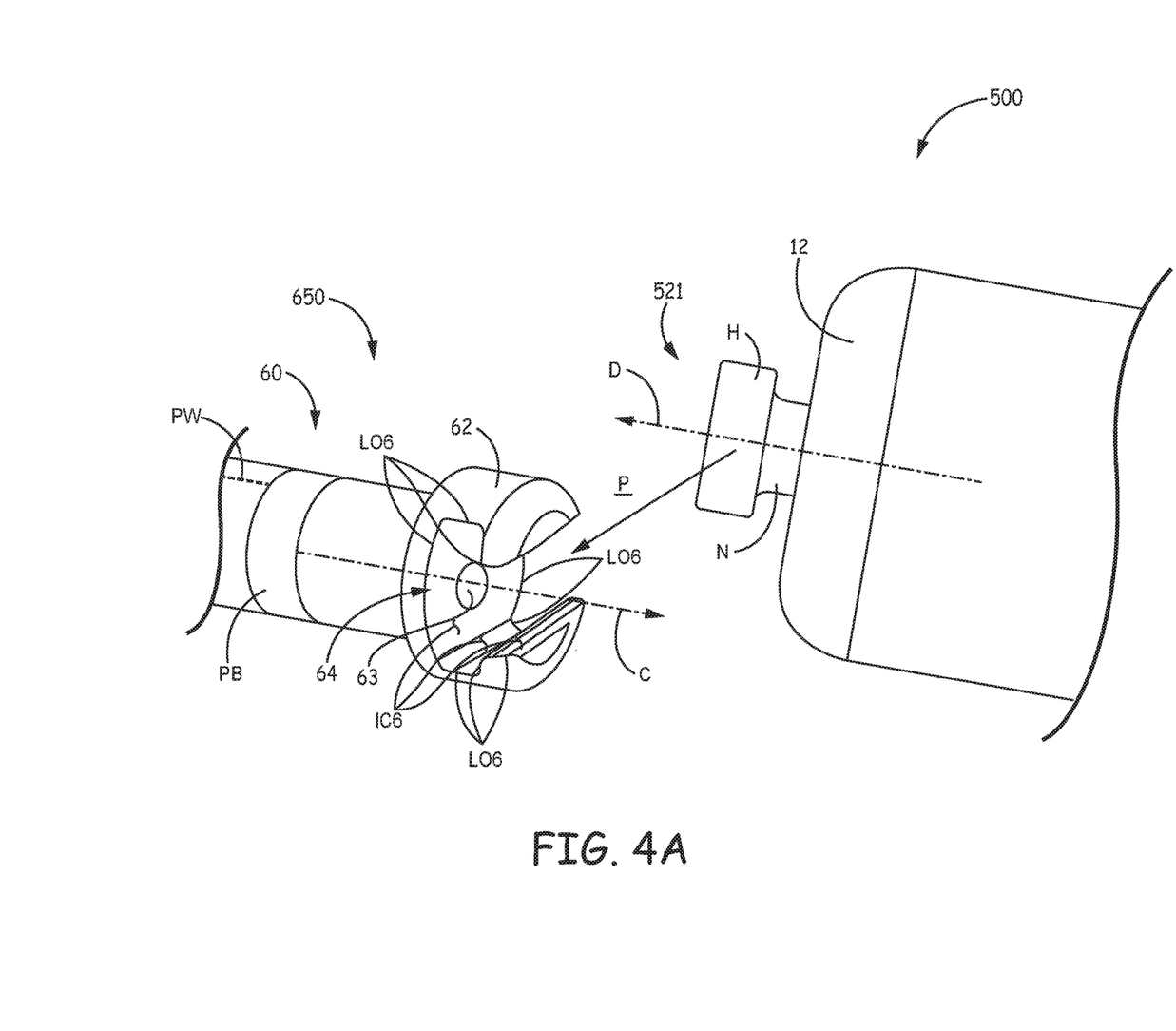
FIGS. 4A-B are perspective views of a distal portion of a catheter assembly and a proximal portion of an associated implantable medical device, according to some alternate embodiments.
Figure 4B:
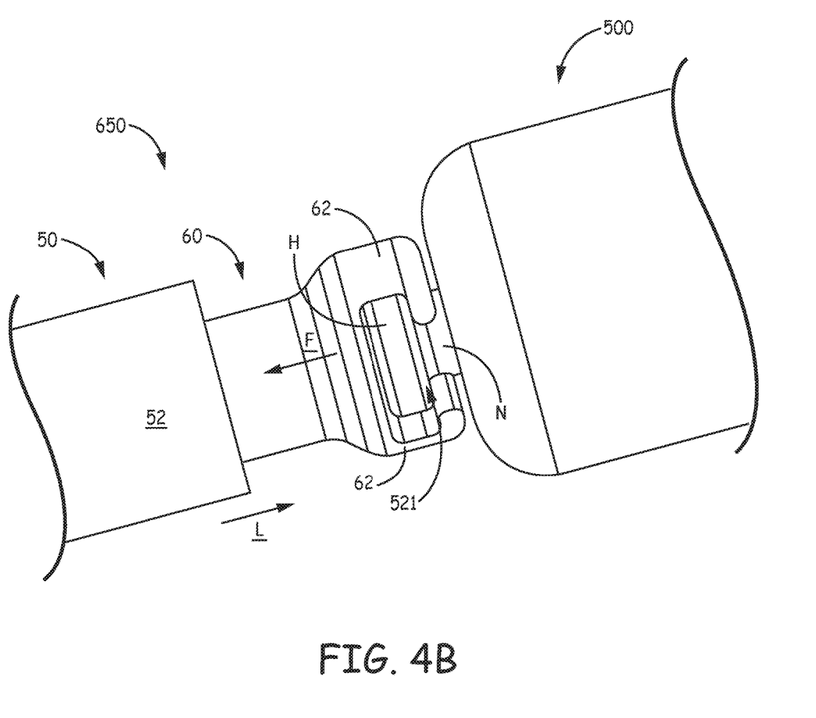

FIGS. 4A-B are perspective views of a distal portion of catheter inner assembly 650 and a proximal portion of associated implantable medical device 500, according to some alternate embodiments. FIGS. 4A-B illustrate the head and neck contour of device holding member 521 being slightly different than that of device holding member 421. FIGS. 4A-B further illustrate a distal end 62 of an elongate shaft 60 of catheter inner assembly 650 exposed and having a receptacle 64 formed therein that conforms to head H and neck N of holding member 521. With reference to FIG. 4A, receptacle 64 has an interior contour IC6 configured to mate with the head and neck contour of device holding member 521, when holding member 521 is received therein, for example, as shown in FIG. 4B. Receptacle 64 may receive device holding member 521 through one of a pair of laterally facing openings thereof, each of which has a profile LO6 matching a longitudinal profile of head H and neck N of holding member 521, the longitudinal profile extending along longitudinal axis D of device 500. As in FIG. 3A, FIG. 4A shows longitudinal axis C of catheter inner assembly 650 to provide a reference for the orientation of each of the pair of laterally facing openings of receptacle 64 (that is, facing in a direction approximately orthogonal to axis C), and to show that openings are located directly opposite one another and aligned with one another.

According to the illustrated embodiment, profile LO6 of each laterally facing opening of receptacle 64 allows only properly oriented passage of holding member 521 therethrough, for example, per arrow P of FIG. 4A; and the passage of holding member 521 into receptacle 64 does not cause either to deform. With reference to FIG. 4B, in conjunction with FIGS. 2A-B, inner assembly 650 includes lock and release member 50, which operates in the same manner described above for inner assembly 350, being retractable (per arrow R of FIG. 2A) and advanceable (per arrow L of FIG. 4B) relative to shaft 60. Thus, after holding member 521 has been passed through one of the pair of laterally facing openings of receptacle 64, so that the head and neck contour of holding member 521 mates with interior contour IC6, as shown in FIG. 4B, arcuate sidewall 52 of lock and release member 50 may be moved per arrow L to overlay the openings of receptacle 64 and thereby secure device 500 to catheter 300. As was described above for device 400, once device 500 is secured, outer tubular member 320 may be advanced, per arrow A of FIG. 2A, relative to inner assembly 650 and the secured device 500, so that the distal portion of inner assembly 650 and secured device 500 are contained within lumen 302 of outer tubular member 320, as shown in FIG. 5.

Figure 5:
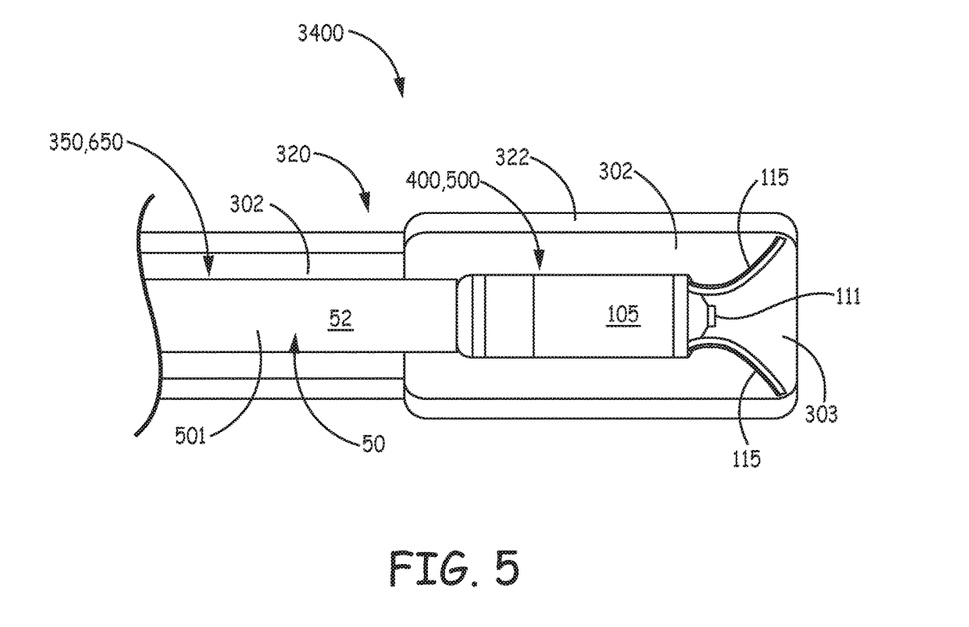
FIG. 5 is a longitudinal cross-section view through a distal portion of a system, according to any of the embodiments described above.

FIG. 5 is a longitudinal cross-section view through a distal portion of system 3400, according to any of the embodiments described above and below. FIG. 5 illustrates secured device 400, 500 having been passed through distal-most opening 303 to be contained within lumen 302 at distal end 322 of outer tubular member 320, such that outer tubular member 320 holds elastically deformable fingers 115 of the device fixation member in an extended condition. According to an exemplary embodiment, fingers 115, which may number up to as many as eight, are formed from a super-elastic material, for example, having been cut from a Nitinol tube according to methods known in the art. After cutting the Nitinol tubing, fingers 115 may be shaped by bending and holding fingers 115 in the relaxed curvature shown in FIG. 2A, while heat treating, according to methods known to those skilled in the art. Fixation fingers 115 may be mounted around electrode 111, for example, in a manner similar to that described for a fixation component 102 in a commonly assigned United States Patent Application 2012/0172690, which description is hereby incorporated by reference. The super-elastic nature of Nitinol allows fingers 115 to elastically deform between the relaxed condition of FIG. 2A and the extended condition of FIG. 5, in which a free end of each finger 115 extends distally away from device housing 105. Thus, an operator can employ catheter 300 to deliver secured device 400, 500, which is contained within lumen 302 of outer tubular member 320, to a target implant site, for example, the site in the right ventricle RV shown in FIG. 1, with fixation member fingers 115 oriented to pierce into tissue at the implant site as the operator retracts outer tubular member 320 relative to inner assembly 350, 550 and secured device 400, 500, for example, by moving first control member 371 toward the second position shown in FIG. 2A.

The piercing fingers 115 are configured to secure electrode 111 in intimate tissue contact at the target implant site, and, according to some embodiments, device 400, 500 preferably includes a steroid-eluting member (not shown), for example, mounted in, or around electrode 111, which is useful for reducing inflammation of the pierced tissue to maintain effective and efficient pacing via electrode 111. Once the operator deploys device 400, 500 with fixation member fingers 115 securing electrode to tissue at the implant site, the operator may apply a pull force through catheter 300 to test the fixation of device 400, 500 at the implant site, and/or remove device 400, 500 from the implant site for repositioning at a more suitable site, if necessary. With reference back to FIGS. 3A-B and FIGS. 4A-B, it may be appreciated that such a force, represented by arrow F (FIGS. 3B, 4B), is transferred to device 400, 500, through holding member 421, 521, by the conforming/mating interior contour IC3, IC6 of receptacle 34, 64. If satisfied with the implant site, the operator can retract lock and release member 50 of inner assembly 350, 650, so that arcuate sidewall 52 at the distal end thereof no longer covers the laterally facing opening(s) of receptacle 34, 64, thereby releasing device 400, 500 from catheter 300 by allowing device holding member 421, 521 to pass through the opening and out from receptacle 34, 64.

With reference back to FIGS. 3A and 4A, a lumen 33, 63 of inner assembly shaft 30, 60 may extend along the entire length thereof, for example, being in fluid communication with receptacle 34, 64 at distal end 32, 62, and in fluid communication with a proximal port opening 376 of handle 370 (FIG. 2A), for example, via a conduit shown with dashed lines in FIG. 2B. A diameter of lumen 33, 63 may range from approximately 0.065 inch to approximately 0.085 inch, for example, to receive passage therethrough of a goose neck snare tool, such as is known to those skilled in the art, which may be useful in retrieving the released device 400, 500 from the implant site, if necessary. An outer diameter of the length of shaft 30, 60 may be approximately 0.11 inch, in some exemplary embodiments.

Furthermore, in some exemplary embodiments, either of inner assemblies 350, 650 may include a steering subassembly, according to any suitable configuration known in the art. With reference to FIGS. 2A-B, FIG. 3A, and FIG. 4A, the optional steering subassembly is shown including an elongate pull wire PW and a pull band PB, wherein pull wire PW extends along a length of shaft 30, 60 with a proximal end thereof coupled to a third control member 373 of handle 370, and a distal end thereof coupled to pull band PB, which is mounted around shaft 30, 60 in proximity to distal end 32, 62. Pull wire PW may extend in another lumen of shaft 30, 60, which extends alongside lumen 33, 63 and has a diameter of approximately 0.016 inch. According to some methods, an operator moves third control member 373 to deflect inner assembly 350, 650, via pull wire PW, when navigating catheter 300 to the target implant site. According to some other exemplary embodiments, rather than being integrated into inner assembly 350, 650, a steering assembly is integrated into outer tubular member 320 in a similar fashion to that described above, according to methods known in the art.

Finally some additional construction detail, according to some exemplary embodiments of catheter 300, is as follows.

Outer tubular member 320, for example, extending over a length of approximately 100 cm, may be formed by a stainless steel braid-reinforced medical grade polymer, for example, one or more appropriate grades of polyether block amide, which are arranged for decreasing stiffness from handle 370 to distal end 322 (e.g., including PEBAX® 3533, 6333, 4033, and 7233), and lumen 302 of tubular member 320 may have a diameter of up to approximately 0.3 inch (7.6 mm) at distal end 322. Distal end 322 may have a radiopaque filler blended therein, or a radiopaque marker (e.g., Tungsten-filled Vestamid®) bonded thereto, either according to methods known to those skilled in the art. In these exemplary embodiments, inner assembly shaft 30, 60 may also have a length being formed from a stainless steel braid-reinforced medical grade polymer, for example, one or more appropriate grades of polyether block amide (e.g., including PEBAX® 3533, 6333, 4033), wherein distal end 32, 62 may formed separately from the length, for example, also from a polyether block amide, such as PEBAX® 7233, that is over-molded onto the length, or molded separately and heat fused to the length. According to some embodiments, distal end 32, 62 is radiopaque for fluoroscopic visualization, for example, being formed from a material that includes a radiopaque filler, such as PEBAX® 7233 blended with 20% to 60% Barium Sulfate.

With reference to FIG. 5, lock and release member 50 of inner assembly 350, 650, according to some embodiments, includes an elongate tube 501 joining proximal end 51 to the distal end thereof, wherein tube 501 may encompass arcuate sidewall 52 that forms the distal end. According to some preferred embodiments, tube 501 is relatively flexible between the proximal and distal ends, for example, being formed from a relatively soft grade of medical grade polyether block amide, such as PEBAX® 3533 or PEBAX® 5533, with stainless steel braid reinforcement. Arcuate sidewall 52 of lock and release member 50 may be significantly stiffer than tube 501 and sufficient to ensure retention of device holding member 421, 521 within receptacle 34, 64, wherein sidewall 52 may be formed from a harder durometer material, such as a medical grade polyamide or the aforementioned PEBAX® 7233 that is over-molded or heat fused to tube 501.

In the foregoing detailed description, the invention has been described with reference to specific embodiments. However, it may be appreciated that various modifications and changes can be made without departing from the scope of the invention as set forth in the appended claims.

For example, the following Items are illustrative of further embodiments:

Item 1. An interventional medical system comprising a relatively compact implantable medical device and a catheter; the medical device comprising an electronic controller, a hermetically sealed housing containing the controller, an electrode electrically coupled to the controller and mounted in proximity to a distal end of the housing, a fixation member mounted to the distal end of the housing, and a holding member, the holding member having a contour that forms a neck and an enlarged head, the neck extending longitudinally from a proximal end of the housing to the head; the catheter comprising an elongate inner assembly, an elongate outer tubular member, and a handle, the handle comprising a first control member and a second control member, the outer tubular member comprising a proximal end coupled to the first control member, the outer tubular member defining an elongate lumen that extends from a proximal opening thereof, at the proximal end of the tubular member, to a distal-most opening thereof, at a distal end of the outer tubular member, the distal-most opening allowing passage of the medical device therethrough, the inner assembly extending along, and being in sliding engagement within the lumen of the outer tubular member; and the catheter inner assembly comprising:

an elongate shaft including a proximal end secured to the handle, and a distal end having a receptacle formed therein, the receptacle being sized to receive the device holding member and having an interior contour configured to mate with the contour of the device holding member when the holding member is received therein, and the receptacle including a laterally facing opening, the laterally facing opening having a profile that matches a longitudinal profile of the neck and enlarged head of the device holding member so that the laterally facing opening allows only a properly oriented passage of the holding member therethrough, the passage being without deformation of either the device holding member or the laterally facing opening of the receptacle; and a lock and release member extending alongside the elongate shaft, the lock and release member including a proximal end and a distal end, the proximal end of the lock and release member being coupled to the second control member of the handle, and the distal end comprising an arcuate sidewall in sliding engagement around the shaft; and wherein, when the second control member of the catheter handle is in a first position, the arcuate sidewall of the distal end of the lock and release member overlays the laterally facing opening of the shaft receptacle;

when the second control member of the catheter handle is in a second position, the arcuate sidewall of the distal end of the lock and release member is located proximal to the laterally facing opening of the shaft receptacle;

when the first control member of the catheter handle is in a first position, the distal end of the shaft and the lock and release member of the inner assembly is contained within the lumen of the outer tubular member of the catheter; and when the first control member of the catheter handle is in a second position, the inner assembly protrudes distally from the distal-most opening of the lumen of the outer tubular member of the catheter.

Item 2. The system of item 1, wherein the handle of the catheter further comprises a third control member; and the inner assembly of the catheter further comprises a steering subassembly, the steering subassembly comprising an elongate pull wire and a pull band, the pull wire extending along a length of the shaft and including a proximal end coupled to the third control member of the handle and distal end coupled to the pull band, the pull band being mounted around the shaft just proximal to the distal end thereof.

Item 3. The system of any one of items 1-2, wherein the laterally facing opening of the receptacle of the inner assembly shaft is a first opening of a pair of laterally facing openings; and a second opening of the pair is located directly opposite the first opening, being aligned therewith, the second opening having a profile that is identical to that of the first opening.

Item 4. The system of any one of items 1-3, wherein at least a portion of the contour of receptacle of the inner assembly shaft is approximately hemispherical.

Item 5. The system of any one of items 1-4, wherein the distal end of the inner assembly shaft is radiopaque.

Item 6. The system of any one of items 1-5, wherein inner assembly lock and release member further includes an elongate tube joining the proximal end thereof to the distal end thereof, the tube extending around the inner assembly shaft, and the arcuate sidewall of the distal end being significantly stiffer than the tube.

Item 7. A catheter assembly useful for securing an implantable medical device to the catheter, the device comprising an electronic controller, a hermetically sealed housing containing the controller, and a holding member, the holding member having a contour that forms a neck and an enlarged head, the neck extending longitudinally from a proximal end of the housing to the head, and the assembly comprising:

a handle comprising a control member;
an elongate shaft including a proximal end secured to the handle, and a distal end having a receptacle formed therein, the receptacle being sized to receive the device holding member and having an interior contour configured to mate with the contour of the device holding member when the holding member is receive therein, and the receptacle including a laterally facing opening, the laterally facing opening having a profile that matches a longitudinal profile of the neck and enlarged head of the device holding member so that the laterally facing opening allows only a properly oriented passage of the holding member therethrough, the passage being without deformation of either the device holding member or the laterally facing opening of the distal end receptacle; and
a lock and release member extending alongside the elongate shaft, the lock and release member including a proximal end and a distal end, the proximal end of the lock and release member being coupled to the control member of the handle, and the distal end comprising an arcuate sidewall in sliding engagement around the shaft; and
wherein, when the control member of the handle is in a first position, the arcuate sidewall of the distal end of the lock and release member overlays the laterally facing opening of the shaft receptacle; and
when the control member of the handle is in a second position, the arcuate sidewall of the distal end of the lock and release member is located proximal to the laterally facing opening of the shaft receptacle.

Item 8. The assembly of items 7, wherein the laterally facing opening of the shaft receptacle is a first opening of a pair of laterally facing openings; and a second opening of the pair is located directly opposite the first opening, being aligned therewith, the second opening having a profile that is identical to that of the first opening.

Item 9. The assembly of any one of items 7-8, wherein at least a portion of the contour of the shaft receptacle is approximately hemispherical.

Item 10. The assembly of any one of items 7-9, wherein the distal end of the shaft is radiopaque.

Item 11. The assembly of any one of items 7-10, wherein the lock and release member further includes an elongate tube joining the proximal end thereof to the distal end thereof, the tube extending around the shaft, and the arcuate sidewall of the distal end being significantly stiffer than the tube.

Item 12. A method for securing an implantable medical device to a catheter, the medical device comprising an electronic controller, a hermetically sealed housing containing the controller, an electrode electrically coupled to the controller and mounted in proximity to a distal end of the housing, a fixation member mounted to the distal end of the housing, and a holding member, the holding member having a contour that forms a neck and an enlarged head, the neck extending longitudinally from a proximal end of the housing to the head, and the method comprising:
positioning the device adjacent to a laterally facing opening of a receptacle of the catheter so that a longitudinal profile of the neck and enlarged head of the device holding member is oriented to coincide with a matching profile of the laterally facing opening;
passing the positioned device holding member through the laterally facing opening of the catheter receptacle so that the contour of the holding member mates with an interior contour of the catheter receptacle; and
advancing an arcuate sidewall of the catheter, after the device holding member mates with the interior contour of the catheter receptacle, until the sidewall overlays the laterally facing opening of the catheter receptacle; and
wherein, passing the positioned device holding member through the laterally facing opening of the catheter receptacle does not deform the holding member or the opening.

Item 13. The method of item 12, further comprising:
retracting an outer tubular member of the catheter relative to the receptacle of the catheter prior to positioning the device adjacent to the laterally facing opening of the receptacle, the receptacle being formed in a distal end of an elongate shaft, around which the outer tubular member extends; and
advancing the outer tubular member relative to the receptacle, after advancing the arcuate sidewall, until the outer tubular member extends around the device and holds the fixation member thereof in an extended condition.

Item 14. The method of any one of items 12-13, wherein:
retracting the outer tubular member comprises moving a first control member of a handle of the catheter in a first direction;
advancing the arcuate sidewall comprises moving a second control member of the catheter handle; and
advancing the outer tubular member comprises moving the first control member in a second direction, the second direction being opposite the first direction.

We claim:

1. An interventional medical system comprising:
an implantable medical device comprising an electronic controller, a hermetically sealed housing containing the controller, an electrode electrically coupled to the controller, a fixation member mounted to a distal end of the housing, and a holding member having a first contour;
a catheter comprising:
an elongate outer tubular member defining an elongate lumen that extends from a proximal opening at a proximal end of the tubular member to a distal-most opening at a distal end of the outer tubular member, the distal-most opening allowing passage of the medical device therethrough,
a handle comprising a first control member and a second control member, and
an elongate inner assembly in sliding engagement within the lumen of the outer tubular member, the inner assembly comprising:
an elongate shaft including a proximal end secured to the handle and a distal end having a receptacle formed therein, the receptacle being sized to receive the device holding member and having an interior contour configured to mate with the contour of the device holding member when the holding member is received therein, and the receptacle including a laterally facing opening having a profile that matches a longitudinal profile of the first contour of the device holding member such that when the receptacle receives the device holding member the receptacle constrains the medical device such that the receptacle only enables the medical device to move in a lateral direction along the lateral facing opening relative to a longitudinal axis of the elongate shaft without deformation of either the device holding member or the laterally facing opening of the receptacle; and a lock and release member extending alongside the elongate shaft that includes a proximal end that is coupled to the second control member of the handle and a distal end that comprises a sidewall in sliding engagement around the shaft, wherein the elongate inner assembly is configured to move the sidewall of the distal end of the lock and release member from a first configuration in which the sidewall overlays the laterally facing opening of the shaft receptacle to a second configuration where the sidewall is located proximal to the laterally facing opening of the shaft receptacle when the second control member of the catheter handle is moved from a first position to a second position, wherein the elongate inner assembly is configured such that the distal end of the shaft and the lock and release member is contained within the lumen of the outer tubular member of the catheter when the first control member of the catheter handle is in a first position, and wherein the elongate inner assembly is configured such that the inner assembly protrudes distally from the distal-most opening of the lumen of the outer tubular member of the catheter when the first control member of the catheter handle is in a second position.

2. The system of claim 1, wherein the handle of the catheter further comprises a third control member, and the inner assembly of the catheter further comprises a steering subassembly, the steering subassembly comprising an elongate pull wire and a pull band, the pull wire extending along a length of the shaft and including a proximal end coupled to the third control member of the handle and a distal end coupled to the pull band, the pull band being mounted around the shaft just proximal to the distal end thereof.

3. The system of claim 1, wherein the laterally facing opening of the receptacle of the inner assembly shaft is a first opening of a pair of laterally facing openings, and a second opening of the pair is located directly opposite the first opening, being aligned therewith, the second opening having a profile that is identical to that of the first opening.

4. The system of claim 1, wherein at least a portion of the contour of the receptacle of the inner assembly shaft is approximately hemispherical.

5. The system of claim 1, wherein the distal end of the inner assembly shaft is radiopaque.

6. The system of claim 1, wherein the inner assembly lock and release member further includes an elongate tube joining the proximal end thereof to the distal end thereof, the tube extending around the inner assembly shaft, and the sidewall of the distal end being significantly stiffer than the tube.

7. The system of claim 1, wherein the first contour forms a neck and an enlarged head, the neck extending longitudinally from a proximal end of the housing to the head.

8. A catheter assembly useful for securing an implantable medical device to the catheter assembly, the implantable medical device comprising an electronic controller, a hermetically sealed housing containing the controller, and a holding member, the holding member having a first contour, and the catheter assembly comprising:
a handle comprising a control member;
an elongate shaft including a proximal end secured to the handle and a distal end having a receptacle formed therein, the receptacle being sized to receive the device holding member and having an interior contour configured to mate with the contour of the device holding member when the holding member is received therein, and the receptacle including a laterally facing opening, the laterally facing opening having a profile that matches a longitudinal profile of the first contour of the device holding member such that when the receptacle receives the device holding member the receptacle constrains the medical device such that the receptacle only enables the medical device to move in a lateral direction along the lateral facing opening relative to a longitudinal axis of the elongate shaft without deformation of either the device holding member or the laterally facing opening of the distal end receptacle;
a lock and release member extending alongside the elongate shaft that includes a proximal end coupled to the control member of the handle and a distal end comprising a sidewall in sliding engagement around the shaft,
wherein the elongate inner assembly is configured to move the sidewall of the distal end of the lock and release member from a first configuration in which the sidewall overlays the laterally facing opening of the shaft receptacle to a second configuration where the sidewall is located proximal to the laterally facing opening of the shaft receptacle when the second control member of the handle is moved from a first position to a second position.

9. The assembly of claim 8, wherein the laterally facing opening of the shaft receptacle is a first opening of a pair of laterally facing openings, and a second opening of the pair is located directly opposite the first opening, being aligned therewith, the second opening having a profile that is identical to that of the first opening.

10. The assembly of claim 8, wherein at least a portion of the contour of the shaft receptacle is approximately hemispherical.

11. The assembly of claim 8, wherein the distal end of the shaft is radiopaque.

12. The assembly of claim 8, wherein the lock and release member further includes an elongate tube joining the proximal end thereof to the distal end thereof, the tube extending around the shaft, and the sidewall of the distal end being significantly stiffer than the tube.

13. The assembly of claim 8, wherein the first contour forms a neck and an enlarged head, the neck extending longitudinally from a proximal end of the housing to the head.

14. A method for securing an implantable medical device to a catheter,
wherein the implantable medical device comprises an electronic controller, a hermetically sealed housing containing the electronic controller, an electrode electrically coupled to the electronic controller and mounted in proximity to a distal end of the housing, a fixation member mounted to the distal end of the housing, and a holding member having a first contour,
wherein the catheter comprises:
an elongate outer tubular member defining an elongate lumen that extends from a proximal opening at a proximal end of the tubular member to a distal-most opening at a distal end of the outer tubular member, the distal-most opening allowing passage of the medical device therethrough;
a handle comprising a first control member and a second control member; and
an elongate inner assembly in sliding engagement within the lumen of the outer tubular member,
the inner assembly comprising:
an elongate shaft including a proximal end secured to the handle and a distal end having a receptacle formed therein, the receptacle being sized to receive the holding member and having an interior contour configured to mate with the contour of the holding member when the holding member is received therein, and the receptacle including a laterally facing opening having a profile that matches a longitudinal profile of the first contour of the holding member such that when the receptacle receives the holding member the receptacle constrains the implantable medical device such that the receptacle only enables the implantable medical device to move in a lateral direction along the lateral facing opening relative to a longitudinal axis of the elongate shaft without deformation of either the holding member or the laterally facing opening of the receptacle; and a lock and release member extending alongside the elongate shaft that includes a proximal end that is coupled to the second control member of the handle and a distal end that comprises a sidewall in sliding engagement around the elongate shaft, the method comprising:

positioning the implantable medical device adjacent to the laterally facing opening of the receptacle so that the longitudinal profile of the first contour of the holding member is oriented to coincide with the matching longitudinal profile of the laterally facing opening;

passing the positioned holding member through the laterally facing opening of the receptacle so that the contour of the holding member mates with the interior contour of the receptacle such that the implantable medical device can only move in a lateral direction along the laterally facing opening relative to a longitudinal axis of the catheter; and advancing the lock and release member, after the holding member mates with the interior contour of the receptacle, until the lock and release member overlays the laterally facing opening of the receptacle; and wherein, passing the positioned holding member through the laterally facing opening of the receptacle does not deform the holding member or the opening.

15. The method of claim 14, further comprising: retracting an outer tubular member of the catheter relative to the receptacle of the catheter prior to positioning the device adjacent to the laterally facing opening of the receptacle, the receptacle being formed in a distal end of an elongate shaft, around which the outer tubular member extends; and advancing the outer tubular member relative to the receptacle, after advancing the sidewall, until the outer tubular member extends around the device and holds the fixation member thereof in an extended condition.

16. The method of claim 15, wherein:

retracting the outer tubular member comprises moving a first control member of a handle of the catheter in a first direction;

advancing the sidewall comprises moving a second control member of the catheter handle; and advancing the outer tubular member comprises moving the first control member in a second direction, the second direction being opposite the first direction.

17. The method of claim 14, wherein the first contour forms a neck and an enlarged head, the neck extending longitudinally from a proximal end of the housing to the head.

* * * * *